United States Patent [19]

Fritch et al.

[11] Patent Number: 5,600,009
[45] Date of Patent: Feb. 4, 1997

[54] USE OF 4-SUBSTITUTED 2-BUTANONES TO PREPARE NABUMETONE

[75] Inventors: John F. Fritch; Mohammad Aslam; Dora E. Rios; Joel C. Smith, all of Corpus Christi, Tex.

[73] Assignee: Hoechst Celanese Corporation, Somerville, N.J.

[21] Appl. No.: 629,656

[22] Filed: Apr. 9, 1996

[51] Int. Cl.$^6$ .................................................. C07C 45/62
[52] U.S. Cl. ........................ 568/318; 568/314; 568/315; 568/316
[58] Field of Search .................................... 568/314, 315, 568/316, 318

[56] References Cited

U.S. PATENT DOCUMENTS

| | | | |
|---|---|---|---|
| 4,061,779 | 12/1977 | Lake et al. | 424/331 |
| 4,221,741 | 9/1980 | Gaster | 568/314 |
| 4,420,639 | 12/1983 | Lake et al. | 568/328 |
| 5,225,603 | 7/1993 | Aslam et al. | 568/315 |

FOREIGN PATENT DOCUMENTS

| | | | |
|---|---|---|---|
| 0376516B1 | 2/1993 | European Pat. Off. | C07C 49/255 |
| 8900721 | 10/1989 | Netherlands . | |

OTHER PUBLICATIONS

"Convenient Syntheses of Nabumetone," Aslam et al.; Synthesis Communications, 869, 1989.

*Primary Examiner*—James H. Reamer
*Attorney, Agent, or Firm*—M. Susan Spiering

[57] ABSTRACT

The palladium-catalyzed coupling of aryl and vinyl halides with vinylic compounds is disclosed. A preferred embodiment relating to the palladium catalyzed coupling of 4-substituted and 6-substituted-2-methoxynaphthalene to form nabumetone is also disclosed. The beauty of this novel reaction is that methylvinylketone, normally employed by the art directly as-is for the preparation of nabumetone, is formed in situ. We have discovered a mechanism to take advantage of the in situ formation of methylvinylketone, thus avoiding the use of expensive, toxic, and unstable methyl vinyl ketone feed. This reaction may be employed for a variety of pharmaceutically active and non-pharmaceutical compounds.

28 Claims, No Drawings

USE OF 4-SUBSTITUTED 2-BUTANONES TO PREPARE NABUMETONE

This application claims priority to U.S. Ser. No. 08/473,603 filed on Jun. 6, 1995, now abandoned.

FIELD OF THE INVENTION

This invention relates to pharmaceutically active compounds, a process for preparing and use thereof. More specifically, this invention relates to the synthesis and use of nabumetone.

BACKGROUND OF THE INVENTION 4-(6'-methoxy-2'-naphthyl)but-3-en-2-one (Formula 4), is a valuable intermediate in the manufacture of 4-(6'methoxy-2'-naphthyl)butan-2-one, a nonsteroidal anti-inflammatory known as nabumetone (Formula 1 ).

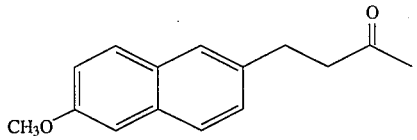

The art has generally prepared nabumetone from palladium (Pd)-catalyzed coupling of 6-bromo-2-methoxynaphthalene (BMON) and methyl vinyl ketone (MVK) in accordance with that described in U.S. Pat. No. 5,225,603, herein incorporated by reference. MVK is costly, has limited (chemical) stability, and toxological concerns associated with it. Alternatives to MVK for the synthesis of nabumetone are sought by the industry.

U.S. Pat. No. 4,061,779 discloses hydrogenation of 4-(6'-methoxy-2'-naphthyl)but-3-en-2-one to yield nabumetone as the final product. However, expensive 6-methoxy-2-naphthaldehyde is used to prepare butanone (4) and is a costly reagent.

Netherlands patent application 8900721 discloses an alternate reaction for the production of nabumetone in which 4-chloro-2-butanone or 4-diethylamino-2-butanone is employed instead of MVK with the heterogeneous catalyst, palladium on carbon. Under the conditions described in Netherlands '721, the 4-substituted-2-butanones yield a diaryl adduct, 4,4,-di(6'-methoxynaphth-2'-yl)but-3-en-2-one, as a major or, in some cases, predominate product.

Thus, methods are sought to obtain nabumetone in high yields, safely, and cost effectively.

SUMMARY OF THE INVENTION

The present invention relates generally to chemical reactions involving the catalyzed, preferably palladium-catalyzed, coupling of aryl and vinyl halides with vinylic compounds. This reaction is typically referred to as the Heck reaction. In the present invention, Heck catalyst is generated in situ using palladium chloride and triphenylphosphine in the presence of an organic solvent, e.g., dimethylformamide.

The present invention employs Heck technology and relates specifically to a process for the preparation of nabumetone (1) comprising contacting substituted butanone

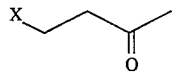

wherein X is $CH_3SO_3$, OR, $NR_2$, or halogen and each R is independently hydrogen, alkyl, aryl, acyl, alkanesulfonyl, arenesulfonyl, carbamoyl, alkoxycarbonyl, or aryloxycarbonyl;

with, substituted methoxynaphthalene

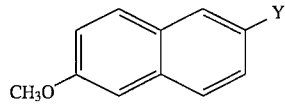

wherein Y=halogen, $N_2^+Z^-$; N=nitrogen; $Z=BF_4^-$, $HSO_4^-$, halide; under suitable reaction conditions, in the presence of a homogeneous catalyst, and subsequently hydrogenating the reaction product to yield

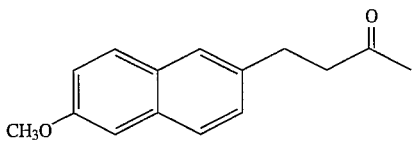

alternatively, the invention comprises comprising contacting

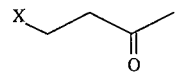

wherein $X=CH_3SO_3$ or OR and each R is independently hydrogen, alkyl, aryl, acyl, alkanesulfonyl, arenesulfonyl, carbamoyl, alkoxycarbonyl, or aryloxycarbonyl;

with, substituted methoxynaphthalene

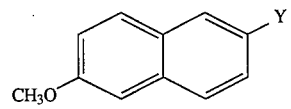

wherein Y=halogen, $N_2^+Z^-$; N=nitrogen; $Z=BF_4^-$, $HSO_4^-$, halide;

under suitable reaction conditions, in the presence of a heterogeneous catalyst to yield 4, and subsequently hydrogenating the reaction product to yield nabumetone (1).

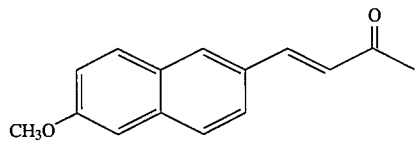

Each reaction described above, whether with homogeneous or heterogeneous catalyst, may be stopped at the conclusion of the coupling reaction between the butanone and the naphthalene derivative and the resultant coupling product isolated.

Suitable reaction conditions generally involve temperatures in the range of about 100°–200° C., pressures in the range of about 0–1500 psi, and reaction times in the range of about 10 min to 24 hrs. A catalyst, preferably a homogeneous palladium catalyst is preferably generated in situ by the coupling of palladium dichloride and triphenylphosphine. The homogeneous or heterogeneous catalyst is present in an amount of about 0.005–1.0 mole % relative to the naphthalene feed. The reaction product of the coupling of butanone and the naphthalene derivative is then hydrogenated (with or without previous isolation) to form the desired product, nabumetone.

DETAILED DESCRIPTION OF THE PREFERRED EMBODIMENT

This invention is concerned with a new process for the preparation of nabumetone without employing costly MVK directly. It has now been found that homogeneous palladium-catalyzed reaction of 2-bromo-6-methoxynaphthalene and 4-substituted 2-butanones produces butenone (4) in high yield,

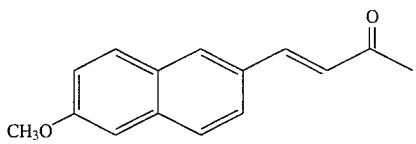

A preferred embodiment of the present invention involves a process for the preparation of nabumetone precursor (4) and subsequent processing to obtain the nabumetone product comprising contacting substituted butanone

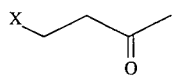

wherein X=$CH_3SO_3$, OR, $NR_2$, or halogen and each R is independently hydrogen, alkyl, aryl, acyl, alkanesulfonyl, arenesulfonyl, carbamoyl, alkoxycarbonyl, or aryloxycarbonyl;

with, substituted methoxynaphthalene

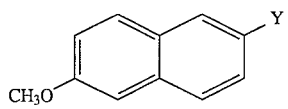

wherein Y=halogen, $N_2^+Z$, N=nitrogen; Z=$BF_4^-$, $HSO_4^-$, halide;

under suitable reaction conditions, in the presence of a homogeneous catalyst, and subsequently hydrogenating the reaction product to yield

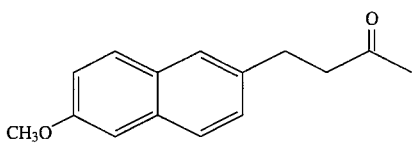

alternatively, the invention comprises the preparation of 4-(6'-methoxy-2'-naphthyl)-but-3-en-2-one comprising contacting substituted butanone

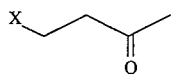

wherein X=$CH_3SO_3$, OR and each R is independently hydrogen, alkyl, aryl, acyl, alkanesulfonyl, arenesulfonyl, carbamoyl, alkoxycarbonyl, or aryloxycarbonyl;

with, substituted methoxynaphthalene

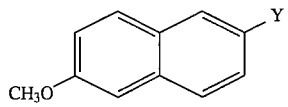

wherein Y=halogen, $N_2^+Z^-$; N=nitrogen; Z=$BF_4^-$, $HSO_4^-$, halide;

under suitable reaction conditions, in the presence of a heterogeneous catalyst, and subsequently hydrogenating the reaction product to yield

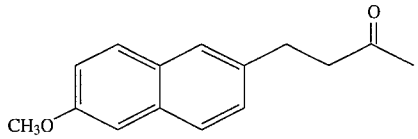

Another embodiment of the present invention is the coupling reaction of 4-substituted phenols of Formula 5

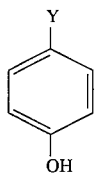

wherein Y is as indicated above, with 4-substituted 2-butanones of Formula 2, under suitable reaction conditions to produce 4-(4'-hydroxyphenyl)but-3-en-2-one and optional hydrogenation of this butanone to 4-(4'-hydroxyphenyl)-2-butanone (raspberry ketone).

An alternate process for the preparation of 4-arylbut-3-en-2-ones comprises contacting under suitable conditions a substituted arene, ArY, a palladium salt, a phosphine ligand compound, and a compound selected from the group consisting of methyl vinyl ketone and 4substituted 2-butanone derivatives, wherein Ar is substituted or unsubstituted phenyl or naphthyl; Y=halogen, $N_2^+Z^-$; N=nitrogen; Z=$BF_4^-$, $HSO_4^-$, halide; X is $CH_3SO_3$, OR or halide, and each R is independently hydrogen, alkyl, aryl, acyl, alkanesulfonyl, arenesulfonyl, carbamoyl, alkoxycarbonyl, or aryloxycarbonyl.

A further alternative process for the preparation of 4-arylbut-3-en-2-ones comprises contacting under suitable conditions or substituted arene, ArY, a homogeneous palladium catalyst, and a 4-substituted 2-butanone derivative,

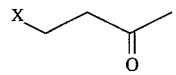

wherein X=$CH_3SO_3$, OR, $NR_2$, or halogen and each R independently hydrogen, alkyl, aryl, acyl, alkanesulfonyl, arenesulfonyl, carbamoyl, alkoxycarbonyl, or aryloxycarbonyl;

with, substituted methoxynaphthalene

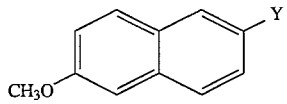

wherein Y=halogen, $N_2^+Z^-$; N=nitrogen; Z=$BF_4^-$, $HSO_4^-$, halide, and Ar is substituted or unsubstituted phenyl or naphthyl.

A still further alternative process for the preparation of 4-arylbut-3-en-2-ones comprises contacting under suitable conditions a substituted arene, ArY, a heterogeneous catalyst, preferably a heterogeneous palladium catalyst, and a 4-substituted 2-butanone derivative, having the following formula

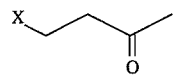

wherein X=$CH_3SO_3$ or OR and each R independently hydrogen, alkyl, aryl, acyl, alkanesulfonyl, arenesulfonyl, carbamoyl, alkoxycarbonyl, or aryloxycarbonyl;

with, substituted methoxynaphthalene

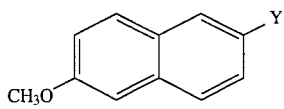

wherein Y=halogen, $N_2^+Z^-$; N=nitrogen; $Z=BF_4^-$, $HSO_4^-$, halide, and Ar is substituted or unsubstituted phenyl or naphthyl, under suitable reaction conditions.

Another alternative relates to a process for preparing 4-arylbut-3-en-2-ones comprising contacting under suitable conditions a solvent, a substituted arene, ArY, and a compound selected from the group consisting of methyl vinyl ketone and a 4-substituted 2-butanone derivative having the following formula

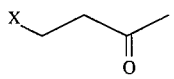

wherein $X=CH_3SO_3$, OR, $NR_2$, or halide and each R independently hydrogen, alkyl, aryl, acyl, alkanesulfonyl, arenesulfonyl, carbamoyl, alkoxycarbonyl, or aryloxycarbonyl; Ar is substituted or unsubstituted phenyl or naphthyl; Y=halogen, $N_2^+Z$, N=nitrogen, $Z=BF_4^-$, $HSO_4^-$, halide to produce a 4-aryl-3-en-2-one and hydrogenating the 4-arylbut-3-en-2-one in the presence of a solvent under suitable conditions, wherein further the 4-arylbut-en-2-one is not isolated prior to the hydrogenation.

Yet another process relates to the preparation of 4-aryl-2-butanone comprising contacting under suitable conditions a 4-arylbut-3-en-2-one, a palladium catalyst, and hydrogen, in the presence or absence of a base.

In the coupling reaction of the arene derivatives with MVK or its 4-substituted 2-butanone substitutes, both the desired monoaryl adduct, 4-arylbut-3-en-2-one, Formula 4, and the undesired diaryl adduct 4,4-diarylbut-3-en-2-one, Formula 6, are formed.

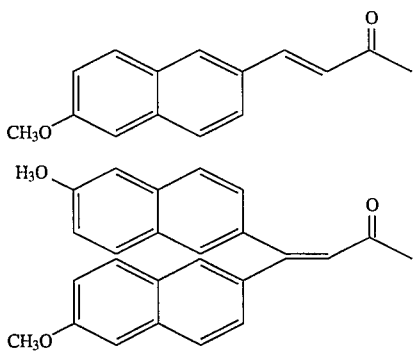

The mono aryl and diaryl adduct products are separated and assayed quantitatively by HPLC. Under reaction conditions which typically yield high monoaryl: diaryl adduct ratios with MVK feed, we have found low monoaryl: diaryl adduct ratios are obtained with MVK substitutes. However, with some reaction modifications we have been able to obtain high monoaryl: diaryl adduct ratios employing MVK substitutes. Particular preferred MVK substitutes for the present invention include 4-hydroxy-2-butanone and 4-acetoxy-2-butanone. We have discovered the surprising results that (1) by appropriate reduction of the amount of catalyst used in coupling reactions employing 4-substituted 2-butanone derivatives, high monoaryl: diaryl adduct ratio results; and (2) the coupling reaction of arenes with 4-substituted 2-butanone derivatives can be advantageously carried out with much less catalyst than is needed for coupling reactions typically employing MVK feed.

Not wishing to be bound by theory, it is believed that the 4-substituted 2-butanones undergo elimination to generate MVK in situ, and that the resulting MVK then undergoes coupling with the arene derivative. It is further believed that although coupling with MVK to monoaryl adduct is inherently faster than coupling with monoaryl adduct to diaryl adduct, that relatively large amounts of diaryl adduct are the result of coupling reactions which have been starved with respect to MVK. Because MVK undergoes competing side reactions, such as dimerization to acetyl-6-methyl-2,3-dihydropyran as well as oligimerization, it is preferred that the rates of MVK generation and the coupling reaction be comparable to minimize formation of diaryl adduct. Techniques generally employed for the present invention to make these rates comparable include using less coupling catalyst than that needed with MVK feed; adding all or a portion of the 4-substituted 2-butanone derivative to the reaction mixture throughout the reaction period rather than all at the beginning; and/or adjustment of reaction temperature. Such techniques are employed as needed to achieve an acceptably high monoaryl: diaryl adduct ratio.

Suitable reaction conditions for the coupling of butanone and naphthyl (or aryl or arene) derivatives are generally chosen based on the specific butanone and aryl derivatives, base, catalyst, and solvent one plans to employ. One of skill in the art can, without undue experimentation determine ideal reaction conditions by performing initial reactions and monitoring the type and amount of byproducts formed. Overall, the range of operating conditions, i.e., temperature, pressure, reaction time, choice of catalyst and amount thereof, choice of base, solvents, etc., for the synthesis of nabumetone may vary and are as described herein, and in U.S. Pat. No. 5,225,603.

Generally, reaction temperature comprises a range of about 100°–200° C., preferably about 125°–175° C., and more preferably about 130°–140° C. Suitable pressure ranges comprise a general range of about 0–1500 psi, a preferred range of about 0–100 psi, and a most preferred range of about 0–30 psi. Suitable reaction times range from about 0.166–24 hrs, preferably about 0.5–8 hrs, and most preferably about 1–3 hrs. It is important to keep in mind that reaction conditions can vary significantly based on the pressure and temperature employed. Provided that the MVK formed in situ is maintained within the reaction vessel, other parameters may vary within the ranges disclosed herein. Maintaining the MVK within the reaction vessel can be accomplished by conventional techniques. For example, utilizing a sealed reactor under pressure, a reflux condenser, etc.

A palladium (II) catalyst, typically a homogenous Pd catalyst, is used for the coupling reaction and form the nabumetone precursor. The Pd catalyst generally results from a Pd (II) salt and a phosphine ligand compound, such as triphenylphosphine and the like. The most preferred catalyst is dichloro bis(triphenylphosphine)palladium (II) formed by the in situ reaction of palladium dichloride and triphenylphosphine. Other homogeneous catalysts may be generated in situ from other reagents such as palladium diacetate with or without a phosphine ligand, tricyclohexylphosphine, tributylphosphine, tributylphosphite, and the like. The catalyst is generally employed in a catalytic amount sufficient to enable the coupling reaction. The amount is chosen based on the nature of the ketone employed. Generally, the catalyst is used in an amount of about 0.005–1.0 mole % relative to the naphthalene or arene feed, preferably in an amount of about 0.01–0.5 mole %, and most preferably in an amount of about 0.015–0.3 mole % relative to the arene feed. In some cases, for example with 4-hydroxy-2-butanone, it is appropriate to add a portion of the 4-substituted 2-butanone to the reaction mixture throughout the reaction period.

Organic solvents to employ may be chosen from the group consisting of dimethylformamide, N,N-dimethylacetamide, N-methylpyrrolidinone, acetamide, and the like.

The coupling reaction generally employs a base, such as potassium- or sodium carbonate, bicarbonate, or acetate, or bases such as triethylamine, and the like. The base acts to neutralize any acid formed from the coupling reaction which may serve to poison the catalyst. However, we have found that use of amines such as triethylamine, although acceptable with catalyst fed as dichlorobis(triphenylphosphine)palladium, prevent in situ generation of that catalyst from palladium dichloride and triphenylphosphine.

4-Acetoxy-2-butanone is a preferred MVK substitute for the coupling reaction and may be charged directly or prepared in situ from 4-hydroxy-2-butanone and either acetic anhydride or acetyl chloride. 4-Hydroxy-2-butanone and 3-oxobutyl mesylate, i.e., 4-mesyloxy-2-butanone are other 4-substituted 2-butanone derivative which have been employed successfully. The better the 4-substituent of the 2-butanone derivative is as a leaving group, the faster MVK will be generated from that 2-butanone derivative. Precautions such as increasing the amount of base must be taken with leaving groups which may cause decomposition of the product or deactivation of the catalyst. Other butanone derivatives which may be employed include 4-diethylamino-, 4-(N,N-dimethylcarbamyloxy)-4-methoxy-, and 4-benzoyloxy-2-butanone.

2-Methoxynaphthalene substituted at the 6 position with a halogen preferably Br and I, most preferably Br, is the preferred aryl derivative for the coupling reaction. Other suitable substituents include diazonium chloride, bromide, bisulfate, tetrafluoroborate and the like. Other aryl derivatives may be employed. For example, the corresponding 4-hydroxyphenyl derivatives may be coupled to 4-(4'-hydroxyphenyl)but-3-en-2-one, which provides raspberry ketone on hydrogenation.

The nabumetone precursor, or 4-arylbut-3-en-2-one coupling reaction product, may be isolated by conventional means such as filtration. The precursor may be precipitated from the reaction mixture by addition of water, filtered, washed with water and dried. Quantitative recovery has been obtained for the precursor from such isolation. Preferably the precursor is carried forward to hydrogenation with a palladium on carbon catalyst without isolation of the 4-arylbut-3-en-2-one intermediate. An advantage of the present invention is that no such isolation is necessary. The coupling reaction mixture with or without filtration of potassium salts is simply carried forward to hydrogenation by addition of the palladium on carbon catalyst and application of hydrogen pressure. Removal of coupling reaction solvent and handling of said intermediate is thus avoided.

Reaction conditions for the hydrogenation, like the coupling, are interdependent. Suitable hydrogenation conditions include a temperature range of about 20°–100° C., a pressure range of about 15–200 psi, and a reaction time of about 0.5–24 hrs. Generally a reaction temperature of about 50° C., pressure of about 65 psi, and reaction time of about three hours is sufficient to complete the conversion of the product of Formula 4 to nabumetone. Pressure is not a critical feature of the hydrogenation reaction, however, it does accelerate the reaction.

During the hydrogenation reaction, nabumetone alcohol by-product, 7

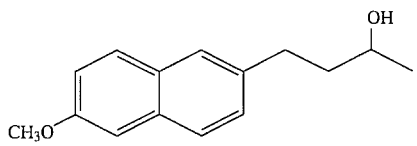

is also formed. It is preferred to maintain the inefficiency to this alcohol by-product at less than 5%. We have found that inclusion of a basic compound such as potassium carbonate, potassium bicarbonate, potassium hydroxide, and the like, or an organic base such as an amine, in the hydrogenation reaction mixture reduces the hydrogenation inefficiency to nabumetone alcohol from an average of about 6% to about 2%. Amounts of potassium in the basic potassium compound preferably range from about 1 to about 200, more preferably about 1 to about 100, and most preferably about 1 to about 50 moles per mole of palladium in the hydrogenation catalyst.

Recrystallization from isopropanol is an effective means for removing nabumetone alcohol from nabumetone. However, recrystallization is not an effective means for removing diaryl adduct or its hydrogenation product, 4,4-di(6'-methoxynaphth-2'-yl)-2-butanone, from nabumetone. We have discovered the surprising result that not only does nabumetone distill under vacuum with very low yield loss, but that such vacuum distillation is an effective means for leaving diaryl adduct and its hydrogenation product behind in the distillation residue. When employing distillation as a purification means, it is preferred to use a sufficiently large diameter heated tube between the distillation and receiving flasks to avoid condensation of the crude nabumetone thereon.

EXAMPLES

The following examples are intended for illustrative purposes only. They are not intended to limit the scope of the invention.

Methyl vinyl ketone (MVK) was purchased from Janssen Chimica. 2-Bromo-6-methoxynaphthalene (BMON) was obtained from Albemarle PPC. Palladium dichloride and 5% palladium on carbon pre-wet to 50 wt % water (Engelhard's ESCAT 111 ) were obtained from Engelhard Corporation. N,N-Dimethylformamide (DMF) was purchased from Air Products. Triphenylphosphine was obtained from Elf Atochem North America. Potassium carbonate was purchased from Armand Products Co. and ground so that 95% passes through a 325 mesh (44 micron) sieve. Hydrogen was purchased from Big Three Industries. Celite 545 was purchased from the Celite Corporation. Isopropanol was purchased from Shell Corporation. 4-Hydroxy-2butanone was purchased from TCI-EP. Acetic anhydride, methanesulfonyl chloride, 4-acetoxy-2-butanone, acetyl chloride, methylene chloride, and triethylamine were purchased from Aldrich Chemical Company.

Example 1: Preparation of Nabumetone Using MVK

Coupling Reaction. BMON (65.16 g), DMF (476.15 g containing 0.5 wt % water; smaller water concentrations work just as well), potassium carbonate (34.01 g), palladium dichloride (12.78 mg), and triphenylphosphine (37.18 mg) were charged to a 1-L 3-neck round bottom flask equipped with a thermocouple in a thermowell, an overhead stirrer, and a reflux condenser connected to a nitrogen and vacuum manifold. The resulting mixture was stirred while the flask was purged by several cycles of evacuation and refilling with nitrogen. Methyl vinyl ketone (27.33 g of 87.3% purity) was then added to the flask by syringe through a slightly separated side arm connection while the flask was kept under a slightly positive pressure of nitrogen. The contents of the reaction flask were then stirred and heated to about 132° C., and the reaction temperature was held constant for about two hours before the contents of the flask were cooled to about 23° C. and suction filtered through 8 micron porosity filter paper. The reaction flask and the filtered potassium salts were washed with two portions of DMF (50.27 g total) and the DMF washes were suction filtered into the coupling reaction mixture flitrate. Approximately 99% of the starting BMON had been converted. Monoaryl adduct: diaryl adduct were observed in a 95.5: 4.5 ratio, as determined by HPLC peak area ratio.

Hydrogenation Reaction. The combined DMF coupling reaction mixture and wash liquor filtrates, 5% palladium on carbon pre-wet to 50 wt % water (1.48 g, 0.35 mmole of palladium), and potassium carbonate (0.04 g) were charged to a 1-L autoclave. The resulting mixture was stirred while the autoclave was purged by three cycles of pressurization with nitrogen to about 50 psig followed by venting to atmospheric pressure. After the stirred autoclave contents had been heated to about 50° C., hydrogen gas was fed from a holding tank to maintain about 65 psi of hydrogen pressure in the autoclave until the stirred autoclave contents stopped consuming hydrogen (about 182 minutes). The autoclave was vented and purged with nitrogen as previously described. Nabumetone and nabumetone alcohol were present in a 98.4: 1.6 F.I.D. G.C. peak area ratio.

Isolation of Crude Nabumetone. The hydrogenation reaction mixture was then suction filtered through 8 micron porosity filter paper. The autoclave and the filtered solids were washed with two portions of DMF (18.79 g total), and the DMF washes were suction filtered into the hydrogenation reaction mixture filtrate. DMF was then removed from the combined DMF hydrogenation reaction mixture and wash liquor filtrates by simple vacuum distillation at about 30.5 torr and the pot temperatures rising to about 100° C. While still molten (about 80°–100° C.), the undistilled material was then suction filtered through 8 micron filter paper to remove potassium salts which had precipitated during the removal of the DMF by vacuum distillation. The filtrate obtained was crude nabumetone.

Distillation of Crude Nabumetone. The crude nabumetone was vacuum distilled. The distilled nabumetone weighed about 54.85 g (87.4% yield). The undistilled material weighed about 9.89 g and contained some nabumetone product.

Recrystallization of Distilled Nabumetone. The distilled nabumetone (54.85 g) was twice recrystallized from three times its weight isopropanol. Yield: about 41.61 g. Purity: greater than about 99.9% pure by HPLC and GC analysis.

Example 2: Preparation of Nabumetone Using 4-Acetoxy-2-butanone

Coupling Reaction. BMON (65.20 g), DMF (469.34 g), potassium carbonate (61.74 g), palladium dichloride (6.26 mg), and triphenylphosphine (18.38 mg) were charged to a 1-L 3neck round bottom flask equipped with a thermocouple in a thermowell, an overhead stirrer, and a reflux condenser connected to a nitrogen and vacuum manifold. The resulting mixture was stirred while the flask was purged by several cycles of evacuation and refilling with nitrogen. 4-Acetoxy-2-butanone (44.87 g) was then added to the flask by syringe through a slightly separated side arm connection while the flask was kept under a slightly positive pressure of nitrogen. The contents of the reaction flask were then stirred and heated to about 132° C., and the reaction temperature maintained for about two hours before the contents of the flask were cooled to about 48.5° C. and suction filtered through 8 micron porosity filter paper. The reaction flask and the filtered potassium salts were washed with two portions of DMF (95.03 g total), and the DMF washes were suction filtered into the coupling reaction mixture filtrate. Approximately 98.9% of the starting BMON had been converted. Mono aryl adduct and diaryl adduct were observed in a 95.5: 4.5 HPLC peak area ratio, and were the only major products observed.

Hydrogenation Reaction. The combined DMF coupling reaction mixture and wash liquor filtrates, 5% palladium on carbon pre-wet to 50 wt % water (1.48 g, 0.35 mmole of palladium), and potassium carbonate (2.09 g) were charged to a 1-L autoclave. The resulting mixture was stirred while the autoclave was purged by three cycles of pressurization with nitrogen to about 50 psig followed by venting to atmospheric pressure. After the stirred autoclave contents had been heated to about 50° C., hydrogen gas was fed from a holding tank to maintain about 65 psi of hydrogen pressure in the autoclave until the stirred autoclave contents stopped consuming hydrogen (about 202 minutes). The autoclave was vented and purged with nitrogen as previously described. The conversion of monoaryl adduct was greater than about 99.7%, and nabumetone and nabumetone alcohol were present in about a 98.96: 1.04 F.I.D. G.C. peak area ratio.

Isolation of Crude Nabumetone. Celite (2.1025 g) was mixed into the hydrogenation reaction mixture, which was then suction filtered through 8 micron porosity filter paper. The autoclave and the filtered solids were washed with two portions of DMF (18.11 g total), and the DMF washes were suction filtered into the hydrogenation reaction mixture filtrate. DMF was then removed from the combined DMF hydrogenation reaction mixture and wash liquor filtrates by simple vacuum distillation at about 30.5 torr and undistilled residue temperatures rising to about 92.3° C. While still molten (80°–100° C.), the undistilled residue was then suction filtered through 8 micron filter paper to remove potassium salts which had precipitated during the removal of the DMF by vacuum distillation. The filtrate was crude nabumetone.

Distillation of Crude Nabumetone. The crude nabumetone was vacuum distilled. The distilled nabumetone weighed about 53.17 g (84.7% yield). The undistilled residue weighed about 8.72 g and contained a significant amount of nabumetone.

Recrystallization of Distilled Nabumetone. The distilled nabumetone (53.17 g) was twice recrystallized by dissolution in isopropanol. The final nabumetone weighed about 40.57 g and was greater than about 99.9% pure by HPLC and GC.

Example 3: Use of 4-Hydroxy-2-butanone Instead of MVK

Example 1 was repeated with the following modifications to the coupling reaction. Before being heated to about 132° C., the coupling reaction mixture charge consisted of BMON (81.19 g), DMF (620 mL), potassium carbonate (42.42 g), palladium dichloride (0.0064 g), triphenylphosphine (0.018 g), and, instead of MVK, 4-hydroxy-2-butanone (24.11 g). Starting at the time the coupling reaction mixture reached about 132° C., more 4-hydroxy-2-butanone (18.43 g) was added by addition funnel from a fourth reaction flask neck over about two hours. Heating and stirring at about 132° C. was continued for a total of about 6.42 hours, at which time approximately 99.4% of the starting BMON had been converted. Mono aryl adduct and diaryl adduct were observed in about a 88.1:11.9 HPLC peak area ratio and were the only major products observed.

Example 4: Use of 4-Hydroxy-2-butanone Instead of MVK

Example 3 was repeated utilizing palladium dichloride (0.009 g), triphenylphosphine (2.77 mg), and 4-hydroxy-2-butanone (10.05 g). Starting at the time the coupling reaction mixture reached about 132° C., more 4-hydroxy-2-butanone (30.92 g) was added by addition funnel from a fourth reaction flask neck over about one hour. Heating and stirring at about 132° C. was continued for a total of about seven hours, at which time about 98.9% of the starting BMON had been converted. Mono aryl adduct and diaryl adduct were observed in a about 89.0:11.0 HPLC peak area ratio and were the only major products observed.

Example 5: Use of 4-Hydroxy-2-butanone and Acetic Anhydride Instead of MVK

Crude 4-acetoxy-2-butanone was prepared as follows. A mixture of 4-hydroxy-2-butanone (101.48 g) and acetic anhydride (131.05 g) was stirred and heated to about 120° C. for about 40 minutes before the acetic acid by-product was removed by vacuum distillation at about 24 torr and vapor temperatures rising to about 49° C. The distillation residue was about 129.0 g of crude 4-acetoxy-2-butanone.

Example 1 was repeated on half scale with the following additional modifications to the coupling reaction. BMON (32.64 g), DMF (250 mL), potassium carbonate (30.92 g), palladium dichloride (3.55 mg), triphenylphosphine (9.23 mg), and, instead of MVK, 22.86 g of the crude 4-acetoxy-2-butanone prepared as just described were charged to a 500 mL round bottom flask and stirred and heated to about 132° C. After about two hours of stirring 99% of the starting BMON had been converted. Mono aryl adduct and diaryl adduct were observed in about a 97.1:2.9 HPLC peak area ratio and were the only major products observed.

Example 6: Use of 4-Hydroxy-2-butanone and Acetyl Chloride Instead of MVK

Example 1 was repeated at half scale with the following additional modifications to the coupling reaction. A 500 mL flask was charged with just DMF (250 mL) and potassium carbonate (31.26 g) before being purged with nitrogen. 4-Hydroxy-2-butanone (15.80 g) instead of MVK was then added by syringe, and the resulting mixture was stirred and cooled to about 0° C. before acetyl chloride (14 mL) was added dropwise over five minutes from an addition funnel in a fourth reaction flask neck. The reaction mixture was then stirred for an additional ten minutes before BMON (32.51 g), palladium dichloride (2.49 mg), and triphenylphosphine (7.07 mg) were added and the resulting mixture was stirred and heated to about 132° C. After about one hour of stirring, 86.7% of the starting BMON had been converted. Mono aryl adduct and diaryl adduct were observed in about a 95.1:4.9 HPLC peak area ratio and were the only major products observed.

Example 7: Use of Crude 4-Mesyloxy-2-butanone Instead of MVK

Crude 4-mesyloxy-2-butanone was prepared as follows. To a stirred, ice-water-bath-cooled mixture of 4-hydroxy-2-butanone (17.30 g), methanesulfonyl chloride (23.01 g), and methylene chloride (100 mL) was added triethylamine (18.91 g) over about 35 minutes by addition funnel at a rate such that the reaction mixture temperature did not exceed about 20° C. The reaction mixture was then stirred at about 0° C. for about one hour before being transferred to a separatory funnel and washed with chilled water (2×100 mL). The resulting methylene chloride phase was dried over $MgSO_4$ and evaporated at room temperature under vacuum to yield an oily residue that was crude 4-mesyloxy-2-butanone.

Example 1 was repeated at quarter scale with the following additional modifications to the coupling reaction. A 250 mL reaction flask was charged with BMON (16.28 g), DMF (124 mL), potassium carbonate (9.49 g), palladium dichloride (0.12 g), triphenylphosphine (0.3508 g), and, instead of MVK, freshly prepared crude 4-mesyloxy-2-butanone (15.50 g). After the reaction mixture had been stirred magnetically at about 132° C. for about two hours, about 24.5% of the starting BMON had been converted. Monoaryl adduct was the only major product observed.

Example 8: Isolation of 4-arylbut-3-en-2-one

Example 6 was repeated with the additional modification that water (550 mL) was added to the combined coupling reaction mixture and wash filtrates to precipitate a yellow solid. After filtration, washing with water (400 mL), and vacuum drying at about 14 torr and about 56° C. for about 72 hours, the solid, crude monoaryl adduct isolated, weighed about 30.96 g (99% crude yield).

These examples illustrate that use of MVK substitutes produce nabumetone in high yield without the direct use of costly unstables and toxic MVK.

Although the present invention is described in terms of nabumetone as the most preferred embodiment, it is conceivable that other compounds may be prepared, without undue experimentation, employing the chemistry described herein.

We claim:
1. A process for the preparation of 4-(6'-methoxy-2'-naphthyl)-but-3-en-2-one comprising contacting a substituted butanone

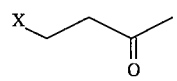

wherein $X=CH_3SO_3$, OR, $NR_2$, or halogen and each R is independently hydrogen, alkyl, aryl, acyl, alkanesulfonyl, arenesulfonyl, carbamoyl, alkoxycarbonyl, or aryloxycarbonyl;

with, substituted methoxynaphthalene

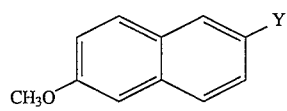

wherein Y=halogen, $N_2^+Z^-$; N=nitrogen; $Z=BF_4^-$, $HSO_4^-$, halide;

wherein the reaction temperature is in the range of about 100°–200° C. the reaction pressure is in the range of about 0–1500 psi, and the reaction time is in the range of about 10 min. to 24 hours. in the presence of a homogeneous palladium catalyst, and subsequently hydrogenating the reaction product to yield

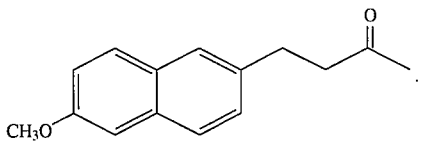

2. A process for the preparation of 4-(6'-methoxy-2'-naphthyl)-but-3-en-2-one comprising contacting

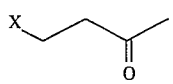

wherein $X=CH_3SO_3$ or OR and each R is independently hydrogen, alkyl, aryl, acyl, alkanesulfonyl, arenesulfonyl, carbamoyl, alkoxycarbonyl, or aryloxycarbonyl;

with, substituted methoxynaphthalene

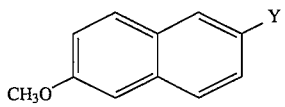

wherein Y=halogen, $N_2^+Z^-$; N=nitrogen; $Z=BF_4^-$, $HSO_4^-$, halide;

wherein the reaction temperature is in the range of about 100°–200° C., the reaction pressure is in the range of about 0–1500 psi, and the reaction time is in the range of about 10 min. to 24 hours, in the presence of a heterogeneous palladium catalyst, and subsequently hydrogenating the reaction product to yield

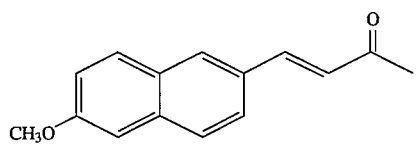

3. The process of claim 2 wherein suitable reaction conditions comprise a temperature in the range about 125°–200° C.

4. The process of claim 3 wherein suitable reaction conditions comprise a temperature in the range of about 130°–140° C.

5. The process of claim 1 comprising a pressure in the range of about 0–30 psi.

6. The process of claim 1 comprising a reaction time in the range of about 0.5–8 hrs.

7. The process of claim 6 wherein suitable reaction conditions comprise a reaction time in the range of about 1–3 hrs.

8. The process of claim 1 or 2 wherein the butanone and the naphthalene compounds are contacted in the presence of a palladium(II) catalyst.

9. The process of claim 1 or 2 wherein said catalyst results from a palladium (II) salt and a phosphine ligand compound.

10. The process of claim 9 wherein the catalyst is dichloro bis-(triphenylphosphine) palladium (II).

11. The process of claim 9 wherein the catalyst is in an amount of about 0.005–1.0 mole % relative to the methoxy naphthalene feed.

12. The process of claim 1 or 2 including an organic solvent chosen from the group consisting of dimethylformamide, N,N-dimethyl acetamide, N-methyl pyrrolidinone, and acetamide.

13. The process of claim 1 or 2 including a base.

14. The process of claim 13 wherein the base is chosen from the group consisting of potassium carbonate, sodium carbonate, potassium acetate, sodium acetate, potassium bicarbonate, sodium bicarbonate, and triethylamine.

15. The process of claim 1 or 2 wherein the hydrogenation reaction occurs in the presence of hydrogen and palladium on carbon catalyst.

16. The process of claim 15 wherein hydrogenation occurs in the presence of a base.

17. The process of claim 1 or 2 further comprising purification of the nabumetone product.

18. The process of claim 17 wherein the nabumetone is purified by recrystallization in isopropanol solvent.

19. The process of claim 17 wherein the nabumetone is purified by vacuum distillation.

20. A process to prepare a nabumetone precursor comprising contacting a butanone

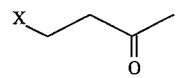

wherein X is $CH_3SO_3$, OR, $NR_2$, or halogen and each R is independently hydrogen, alkyl, aryl, acyl, alkanesulfonyl, arenesulfonyl, carbamoyl, alkoxycarbonyl, or aryloxycarbonyl;

with, substituted methoxynaphthalene

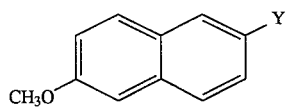

wherein Y=halogen, $N_2^+Z^-$; N=nitrogen; $Z=BF_4^-$, $HSO_4^-$, halide;

wherein the reaction temperature is in the range of about 100°–200° C., the reaction pressure is in the range of about 0–1500 psi, and the reaction time is in the range of about 10 min. to 24 hours, in the presence of a homogeneous palladium catalyst to yield

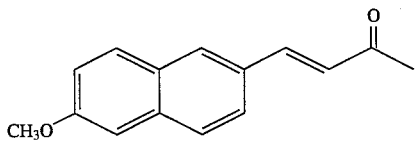

21. A process to prepare a nabumetone precursor comprising contacting

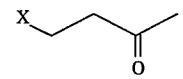

wherein $X=CH_3SO_3$ or OR and each R is independently hydrogen, alkyl, aryl, acyl, alkanesulfonyl, arenesulfonyl, carbamoyl, alkoxycarbonyl, or aryloxycarbonyl;

with, substituted methoxynaphthalene

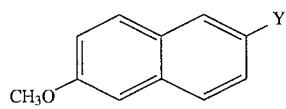

wherein Y=halogen, N₂⁺Z—; N=nitrogen; Z=BF₄—, HSO₄—, halide wherein the reaction temperature is in the range of about 100°–200° C., the reaction pressure is in the range of about 0–1500 psi, and the reaction time is in the range of about 10 min. to 24 hours, in the presence of a heterogeneous palladium catalyst to yield

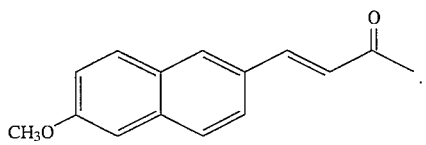

22. A process comprising the coupling reaction of 4-substituted phenols having the following formula

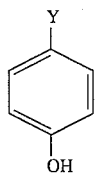

wherein Y is in accordance with claim 1 or 2, with 4-substituted 2-butanones in accordance with claim 1 or 2, wherein the reaction temperature is in the range of about 100°–200° C., the reaction pressure is in the range of about 0–1500 psi, and the reaction time is in the range of about 10 min. to 24 hours, to produce 4-(4'-hydroxy-phenyl)but-3-en-2-one and optional hydrogenation of this butenone to 4-(4'-hydroxyphenyl)-2-butanone.

23. A process for the preparation of 4-arylbut-3-en-2-ones comprising contacting a arene, ArY, a palladium salt, a phosphine ligand compound, and a compound selected from the group consisting of methyl vinyl ketone and 4-substituted 2-butanone derivatives, having the following formula

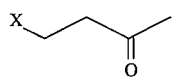

wherein X is CH₃SO₃, or OR, and each R is independently hydrogen, alkyl, aryl, acyl, alkanesulfonyl, arenesulfonyl, carbamoyl, alkoxycarbonyl, or aryloxycarbonyl; Ar is substituted or unsubstituted phenyl, or naphthyl; Y=halogen, N₂⁺Z—; N=nitrogen; Z=BF₄—, HSO₄—, halide;

wherein further the reaction temperature is in the range of about 100°–200° C., the reaction pressure is in the range of about 0–1500 psi, and the reaction time is in the range of about 10 min. to 24 hours, to produce a 4-arylbut-3-en-2-one and subsequently hydrogenating the 4-arylbut-3-en-2-one.

24. The process of claim 23 wherein the phosphine ligand compound is selected from the group consisting of triphenylphosphine, tricyclohexylphosphine, tributylphosphine, and tributylphosphite.

25. A process for the preparation of 4-arylbut-3-en-2-ones comprising contacting a substituted arene, ArY, a homogeneous palladium catalyst, and a 4-substituted 2-butanone derivatives, having the formula

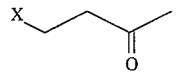

wherein X is CH₃SO₃, OR, or halogen and each R is independently hydrogen, alkyl, aryl, acyl, alkanesulfonyl, arenesulfonyl, carbamoyl, alkoxycarbonyl, or aryloxycarbonyl wherein further the reaction temperature is in the range of about 100°–200– C., the reaction pressure is in the range of about 0–1500 psi, and the reaction time is in the range of about 10 min. to 24 hours;

with, substituted methoxynaphthalene

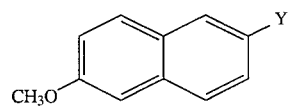

wherein Y=halogen, N₂⁺Z—; N=nitrogen; Z=BF₄—, HSO₄—, halide and Ar is phenyl or naphthyl.

26. A process for the preparation of 4-arylbut-3-en-2-ones comprising contacting a substituted arene, ArY, a heterogeneous palladium catalyst, and a 4-substituted 2-butanone derivatives, having the formula

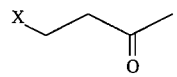

wherein X is CH₃SO₃ or OR, and each R is independently hydrogen, alkyl, aryl, acyl, alkanesulfonyl, arenesulfonyl, carbamoyl, alkoxycarbonyl, or aryloxycarbonyl;

wherein the reaction temperature is in the range of about 100°–200° C., the reaction pressure is in the range of about 0–1500 psi, and the reaction time is in the range of about 10 min. to 24 hours;

with, substituted methoxynaphthalene

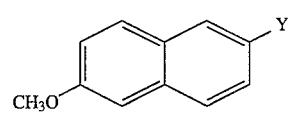

wherein Y=halogen, N₂⁺Z—; N=nitrogen; Z=BF₄—, HSO₄—, halide and Ar is phenyl or naphthyl.

27. The process of claim 1 wherein the substituted butanone is 4-acetoxybutanone and the methoxy naphthylene derivative is 6-bromo-2-methoxynapthalene.

28. The process of claim 1 wherein the butanone is 4-hydroxybutanone and the methoxy naphthylene derivative is 6-bromo-2-methoxynapthalene.

* * * * *